(12) United States Patent
Spellberg et al.

(10) Patent No.: US 11,672,857 B2
(45) Date of Patent: Jun. 13, 2023

(54) COMPOSITIONS AND METHODS FOR A MULTI-ADJUVANT ONLY APPROACH TO IMMUNOPROPHYLAXIS FOR PREVENTING INFECTIONS

(71) Applicant: University of Southern California, Los Angeles, CA (US)

(72) Inventors: Brad Spellberg, Los Angeles, CA (US); Travis Nielsen, Los Angeles, CA (US); Brian Luna, Los Angeles, CA (US)

(73) Assignee: UNIVERSITY OF SOUTHERN CALIFORNIA, Los Angeles, CA (US)

(*) Notice: Subject to any disclaimer, the term of this patent is extended or adjusted under 35 U.S.C. 154(b) by 374 days.

(21) Appl. No.: 16/760,389

(22) PCT Filed: Oct. 29, 2018

(86) PCT No.: PCT/US2018/058045
§ 371 (c)(1),
(2) Date: Apr. 29, 2020

(87) PCT Pub. No.: WO2019/089475
PCT Pub. Date: May 9, 2019

(65) Prior Publication Data
US 2020/0353075 A1 Nov. 12, 2020

Related U.S. Application Data

(60) Provisional application No. 62/578,848, filed on Oct. 30, 2017.

(51) Int. Cl.
| | | |
|---|---|---|
| *A61K 39/00* | (2006.01) | |
| *A61K 39/39* | (2006.01) | |
| *A61K 39/085* | (2006.01) | |
| *A61K 39/104* | (2006.01) | |
| *A61K 36/06* | (2006.01) | |
| *A61K 35/66* | (2015.01) | |
| *A61K 39/108* | (2006.01) | |
| *A61K 39/02* | (2006.01) | |

(52) U.S. Cl.
CPC ............ *A61K 39/39* (2013.01); *A61K 35/66* (2013.01); *A61K 36/06* (2013.01); *A61K 39/025* (2013.01); *A61K 39/0258* (2013.01); *A61K 39/0266* (2013.01); *A61K 39/085* (2013.01); *A61K 39/104* (2013.01); *A61K 39/1045* (2013.01); *A61K 2039/545* (2013.01); *A61K 2039/55505* (2013.01); *A61K 2039/55572* (2013.01); *A61K 2039/55583* (2013.01); *A61K 2039/58* (2013.01)

(58) Field of Classification Search
None
See application file for complete search history.

(56) References Cited

U.S. PATENT DOCUMENTS

| | | | |
|---|---|---|---|
| 5,817,643 A | 10/1998 | Jamas et al. | |
| 9,061,066 B2 | 6/2015 | Gorvel et al. | |
| 9,694,070 B2 | 7/2017 | Gorden et al. | |
| 2006/0068448 A1 | 3/2006 | Takesako et al. | |
| 2006/0165700 A1 | 7/2006 | Ostroff et al. | |
| 2010/0166751 A1 | 7/2010 | Ostroff et al. | |
| 2014/0302076 A1* | 10/2014 | Middelberg | A61K 39/155 435/254.2 |
| 2017/0224811 A1 | 8/2017 | Van Haren et al. | |
| 2017/0239349 A1 | 8/2017 | Agadjanyan et al. | |
| 2021/0299250 A1* | 9/2021 | Levy | A61P 31/16 |
| 2022/0105167 A1* | 4/2022 | Desvaux | A61K 39/0258 |

FOREIGN PATENT DOCUMENTS

WO    WO-2015/161218 A1    10/2015

OTHER PUBLICATIONS

Toussi et al., "Immune Adjuvant Effect of Molecularly-defined Toll-Like Receptor Ligands", Vaccines, Apr. 25, 2014, vol. 2, No. 2, (pp. 323-353).
International Search Report and Written Opinion dated Jan. 15, 2019, from application No. PCT/US2018/058045.

* cited by examiner

*Primary Examiner* — S. Devi
(74) *Attorney, Agent, or Firm* — Foley & Lardner LLP

(57) ABSTRACT

This disclosure provides a new vaccine composition and methods for its use. The composition contains an effective amount of each of: an aluminum hydroxide, a mono-phosphoryl lipid (MPL), and a whole glucan particles (WGP) but no an antigen that raises an immune response against a bacterial or fungal infection.

10 Claims, 8 Drawing Sheets

COMPOSITIONS AND METHODS FOR A MULTI-ADJUVANT ONLY APPROACH TO IMMUNOPROPHYLAXIS FOR PREVENTING INFECTIONS

CROSS-REFERENCE TO RELATED APPLICATION

The present application is a U.S. national stage application under 35 U.S.C. § 371 of International Application No. PCT/US2018/058045, filed Oct. 29, 2018, which in turn claims priority of U.S. Ser. No. 62/578,848, filed Oct. 30, 2017, the entire contents of each of which are incorporated herein by reference in their entireties.

This invention was made with U.S. Government support under R01AI103342 awarded by the National Institutes of Health. The U.S. Government has certain rights in the invention.

BACKGROUND

Throughout this application, several technical publications are referenced by an Arabic numeral. The complete bibliographic citation for each reference is found immediately preceding the claims. The contents of each publication so referenced, and the publications referenced within the specification are hereby incorporated into the present disclosure to more fully describe the state of the art to which this invention pertains.

According to the Center for Disease Control and Prevention (CDC), in 2014, 550,000 Healthcare-Associated Infections (HAIs) occurred in the US, killing tens of thousands of patients and costing ~$100 billion. (1) HAIs are the 6$^{th}$ leading cause of death in the US, ahead of diabetes and kidney disease. (2) Extremely drug-resistant (XDR) Gram-negative bacteria, which are resistant to first-line antibacterial agents (3) and treatable only with agents known to be inferior in efficacy or more toxic than preferred agents, are the highest unmet need for new preventative strategies. Experts have called for new approaches to combatting these infections that are not dependent on behavioral compliance of healthcare providers (e.g. handwashing). (4,5) Therefore, a need exists in the art for safe and effective prevention strategies. This disclosure satisfies this need and provides and related disclosures as well.

SUMMARY OF THE DISCLOSURE

This disclosure provides an entirely new vaccine-derived approach, based on adjuvants without antigen, to mediate broad spectrum short-to-intermediate term protection against deadly, HAIs caused by bacteria (including antibiotic-resistant bacteria) and fungi. This approached is based on entirely new horizontal rather than vertical infection prevention strategy.

Drs. Dick Wenzel and Michael Edmond, two leaders in infection prevention in the US and globally, have described the superiority of so-called "horizontal" rather than "vertical" infection-prevention practices. By "horizontal" they mean approaches that prevent infections caused by many different pathogens at once, which are preferred to approaches that prevent infections one pathogen at a time. (6) This disclosure utilized a horizontal infection prevention strategy by immunizing with broadly-active adjuvants to provide innate immune protection against the Gram-positive and Gram-negative bacterial pathogens.

BRIEF DESCRIPTION OF THE DRAWINGS

FIG. 1A shows how that BALB/c mice vaccinated with various adjuvants and/or proteins were infected IV via the tail-vein] with *S. aureus* LAC (community-acquired MRSA strain). N=8 mice per group. *$p<0.05$ vs. control.

μg)+WGP (30 μg), with only 10 seconds of mixture of Al(OH)₃; mannan was added at a 100 □g dose. Mice were challenged with a higher inoculum of *A. baumannii* HUMC1 (2.4×10⁷ CFUs).

Figure 12:
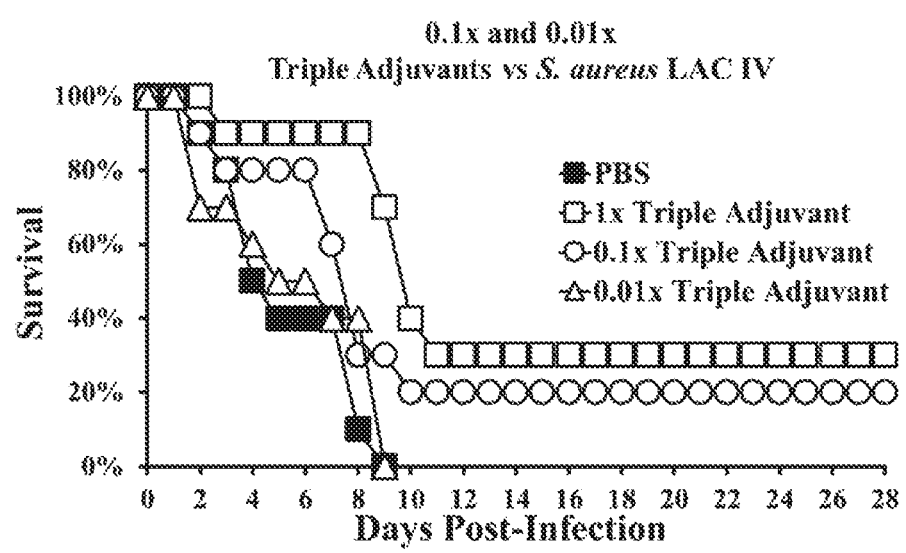

FIG. 12. Mice were administered triple adjuvant=alhydrogel (1.3%)+MPL (10 μg)+WGP (100 μg); 0.1× triple adjuvant=alhydrogel (1.3%)+MPL (1 μg)+WGP (10 μg); 0.01× triple adjuvant=alhydrogel (1.3%)+MPL (0.1 μg)+WGP (1 μg), or PBS. Mice were challenged with *S. aureus* LAC (8.4×10⁷ CFUs).

DETAILED DESCRIPTION

Before the compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All technical and patent publications cited herein are incorporated herein by reference in their entirety. Nothing herein is to be construed as an admission that the invention is not entitled to antedate such disclosure by virtue of prior invention.

The practice of the present invention will employ, unless otherwise indicated, conventional techniques of tissue culture, immunology, molecular biology, microbiology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); MacPherson et al. (1991) PCR 1: A Practical Approach (IRL Press at Oxford University Press); MacPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; Hames and Higgins eds. (1984) Nucleic Acid Hybridization; Anderson (1999) Nucleic Acid Hybridization; Hames and Higgins eds. (1984) Transcription and Translation; Immobilized Cells and Enzymes (IRL Press (1986)); Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; and Mayer and Walker eds. (1987) Immunochemical Methods in Cell and Molecular Biology (Academic Press, London).

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

Definitions

As used in the specification and claims, the singular form "a", "an" and "the" include plural references unless the context clearly dictates otherwise. For example, the term "a cell" includes a plurality of cells, including mixtures thereof.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention.

The term "isolated" as used herein with respect to nucleic acids, such as DNA or RNA, refers to molecules separated from other DNAs or RNAs, respectively that are present in the natural source of the macromolecule. The term "isolated peptide fragment" is meant to include peptide fragments which are not naturally occurring as fragments and would not be found in the natural state. The term "isolated" is also used herein to refer to polypeptides and proteins that are isolated from other cellular proteins and is meant to encompass both purified and recombinant polypeptides. In other embodiments, the term "isolated" means separated from constituents, cellular and otherwise, in which the cell, tissue, polynucleotide, peptide, polypeptide, protein, antibody or fragment(s) thereof, which are normally associated in nature. For example, an isolated cell is a cell that is separated form tissue or cells of dissimilar phenotype or genotype. As is apparent to those of skill in the art, a non-naturally occurring polynucleotide, peptide, polypeptide, protein, antibody or fragment(s) thereof, does not require "isolation" to distinguish it from its naturally occurring counterpart.

A "composition" is intended to mean a combination of the claimed elements and another compound or composition, inert (e.g. a detectable label) or active (with the exclusion of an antigen) alone or in combination with a carrier which can in one embodiment be a simple carrier like saline or pharmaceutically acceptable or a solid support as defined below.

A "pharmaceutical composition" is intended to include the combination of the claimed elements with a carrier, inert or active (with the exclusion of an antigen), making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin (1975) Remington's Pharm. Sci., 15th Ed. (Mack Publ. Co., Easton).

"Administration" can be effected in one dose, continuously or intermittently throughout the course of treatment. Methods of determining the most effective means and dosage of administration are known to those of skill in the art and will vary with the composition used for therapy, the purpose of the therapy, the infection being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and the infecting bacteria or organism. Non-limiting examples of route of administration include oral administration, nasal administration, injection, and topical application.

The term "effective amount" refers to a quantity sufficient to achieve a desired effect. In the context of therapeutic or prophylactic applications, the effective amount will depend on the type and severity of the condition at issue and the characteristics of the individual subject, such as general health, age, sex, body weight, and tolerance to pharmaceutical compositions.

In the case of an in vitro application, in some embodiments the effective amount will depend on the size and nature of the application in question. It will also depend on the nature and sensitivity of the in vitro target and the methods in use. The skilled artisan will be able to determine the effective amount based on these and other considerations. The effective amount may comprise one or more administrations of a composition depending on the embodiment.

The routes of administration applicable to the methods of the invention include intravenous, intranasal, intramuscular, urethrally, intratracheal, subcutaneous, intradermal, topical application, rectal, nasal, oral, inhalation, and other enteral and parenteral routes of administration. Routes of administration may be combined, if desired, or adjusted depending upon the agent and/or the desired effect. An active agent can be administered in a single dose or in multiple doses. Embodiments of these methods and routes suitable for delivery, include systemic or localized routes.

Parenteral routes of administration other than inhalation administration include, but are not limited to, topical, transdermal, subcutaneous, intramuscular, intraorbital, intracapsular, intraspinal, intrasternal, and intravenous routes, i.e., any route of administration other than through the alimentary canal. Parenteral administration can be conducted to effect systemic or local delivery of the inhibiting agent. Where systemic delivery is desired, administration typically involves invasive or systemically absorbed topical or mucosal administration of pharmaceutical preparations.

The term "suffering" as it related to the term "treatment" refers to a subject or patient or individual who has been diagnosed with or is predisposed to a disease or infection. A patient may also be referred to being "at risk of suffering" from a disease or infection. This patient has not yet developed characteristic disease pathology or an active infection, however are known to be predisposed to the disease due to family history, being genetically predispose to developing the disease, being in an environment that puts the subject at substantial risk of being infected, or diagnosed with a disease or disorder that predisposes them to developing the disease to be treated.

Alhydrogel® is a commercially available (Accurate Chemical and Scientific Corporation, Catalogue #A1090S) wet gel colloidal suspension. The InvivoGen catalog (invivogen.com/PDF/Alhydrogel_TDS.pdfd, last accessed on Oct. 23, 2017) describes Alhydrogel® adjuvant as an aluminium hydroxide wet gel suspension. Alhydrogel® particles have a net positive electrical charge at pH 5-7. Alhydrogel® adjuvant 2% is made by Brenntag Biosector, a leader in the global vaccine adjuvants market with a long history of producing high quality products. Alhydrogel® adjuvant 2% was elected as the International Standard Preparation for aluminium hydroxide gels. Alhydrogel® adjuvant 2% is present in multiple commercial vaccine formulations.

Whole glucan particles (WGP) intends particulate formulations of fungal β-glucan. It is a commercially available (InVivoGen Catalogue #tlrl-wgps) powder resuspended in water/saline. This has been used in the past as a vaccine adjuvant.

Mono-phosphoryl lipid (MPL) or lipid A intends a lipid component of an endotoxin held responsible for the toxicity of gram-negative bacteria. It has the chemical structure of:

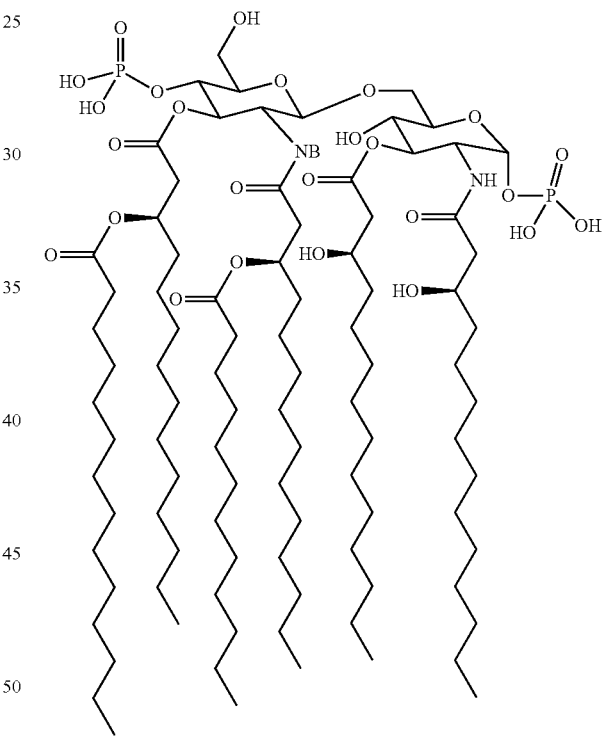

It is commercially available from InVivoGen (Catalog #tlrl-mpls). It has been used as a vaccine adjuvant.

As used herein, the term "mannan" intends polysaccharide found in fungi that is comprised of a mannose polymer (Sigma-Aldrich, catalogue number M7504).

As used herein, the term "antigen that induces an immune response against a bacterial of fungal pathogen" intends for example, conventional vaccine preparations used prophylactically and for treatment of infections and diseases associated with these infections.

As used herein, the term "antigen" intends any substance that causes the body to make an immune response against that substance, Antigens include toxins, chemicals, bacteria, viruses, or other substances that come from outside the body.

Body tissues and cells, including cancer cells, also have antigens on them that can cause an immune response. These antigens can also be used as markers in laboratory tests to identify those tissues or cells. In one aspect, the term "antigen" as claimed herein intends only those which induce an immune response against a bacterial or fungal infection.

A "subject," "individual" or "patient" is used interchangeably herein, and refers to a vertebrate, preferably a mammal, more preferably a human. Mammals include, but are not limited to, murines, rats, rabbits, simians, bovines, ovines, porcines, canines, felines, farm animals, sport animals, pets, equines, and primates, particularly humans.

Compositions

This disclosure provides a composition comprising, or alternatively consisting essentially of, or yet further consisting of, an effective amount of each of: an aluminum hydroxide, a mono-phosphoryl lipid (MPL), and a whole glucan particles (WGP), with the proviso that the composition does not comprise an antigen effective to induce an immune response against a fungal or bacterial pathogen. In a further aspect, the composition further comprises an effective amount of a mannan.

In one aspect, the components are combined to achieve a final concentration. For example, the compositions have an combined concentration in a range from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or altern 0.1 mg/ml to about 1 mg/ml, or alternatively from about 0.2 mg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

The MPL is suspended in a carrier such as a pharmaceutically acceptable carrier such as PBS, to a concentration in a range from about 0.01 mg/ml to about 1 mg/ml, or alternatively from about 0.05 mg/ml to about 1 mg/ml, or alternatively from about 0.1 mg/ml to about 1 mg/ml, or alternatively from about 0.1 mg/ml to about 0.9 mg/ml, or alternatively from about 0.1 mg/ml to about 0.7 mg/ml, or alternatively from about 0.1 mg/ml to about 0.5 mg/ml, or alternatively from about 0.1 mg/ml to about 0.4 mg/ml, or alternatively from about 0.1 mg/ml to about 0.3 mg/ml, or alternatively 0.1 mg/ml to about 0.2 mg/ml, or alternatively from about 0.2 mg/ml to about 0.8 mg/ml, or alternatively from about 0.2 mg/ml to about 0.7 mg/ml, or alternatively from about 0.2 mg/ml to about 0.6 mg/ml, or alternatively from about 0.2 mg/ml to about 0.5 mg/ml, or alternatively from about 0.2 mg/ml to about 0.4 mg/ml, or about 0.2 mg/ml to about 0.3 mg/ml.

The MPL and WGP are then combined in any appropriate combination and it is not intended that the ratios of each component be identical, although they can be combined in a 1:1 ratio. Alternatively the MPL is combined with the WGP in a ratio of about 0.1:1; about 0.2:1; about 0.3:1; about 0.4:1; about 0.5:1; about 0.6:1; or about 0.7:1; or about 0.8:1; or about 0.9:1; or about 1:1. Alternatively the WGP and MPL can combined with the WGP in a ratio of about 0.1:1; about 0.2:1; about 0.3:1; about 0.4:1; about 0.5:1; about 0.6:1; or about 0.7:1; or about 0.8:1; or about 0.9:1; or about 1:1.

After this combination of the MPL and WGP, the combination is further admixed with aluminum hydroxide at about 1:5, or alternatively about 1:6, or alternatively about 1:7, or alternatively about 1:8, or alternatively about 1:9, or alternatively about 1:10, or alternatively about 1:11, or alternatively about 1:12 or alternatively about 1:13, or alternatively about 1:14, or alternatively about 1:15, or alternatively about 1:16, or alternatively about 1:17, or alternatively about 1:18, or alternatively about 1:19 or alternatively about 1:20 ratio.

In some aspect, mannan is dissolved in a carrier such as a pharmaceutically acceptable carrier such as saline, to provide a concentration from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or alternatively from about 0.1 mg/ml to about 1 mg/ml, or alternatively from about 0.2 mg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml. In one aspect, this is added to the triple-component composition.

Alternatively, the aluminum hydroxide and MPL are sourced from a commercial vendor such GlaxoSmithKline (GSK) and combined with mannan and WGP in amounts as noted above.

The compositions can be formulated for in vivo administration (in one or more doses) to administer from about 5 mcg/kg body weight to about 50 mcg/kg body weight, or alternatively 10 mcg/kg body weight to 50 mcg/kg body, or alternatively 20 mcg/kg body weight to about 50 mcg/kg body weight, or alternatively 10 mg/kg body weight to about 100 mcg/kg body weight, or alternatively from about 15 mcg/kg body weight to about 150 mcg/kg body weight, or alternatively from about 20 to mcg/kg body weight to about 200 mcg/kg body weight.

The compositions can be further formulated for storage and distribution such as by lyophilization or freeze-drying. In addition, preservative and stabilizing agents can be added to further enhance the shelf-life of the compositions.

Methods of Treatment

This disclosure also provides methods to enhance immunity in a subject against an infection caused by a bacterial or fungal pathogen by administering to the subject an effective amount of a composition of a composition as described above. The subject to be treated is any animal or human patient at risk of or has developed infection from a bacterial (gram-positive or gram-negative bacteria) or fungus. Non-limiting examples include sport and farm animals, pets and human patients. As used herein, the term "enhance immunity" intends to augment innate immune responses, including macrophage, neutrophil, dendritic cells, and gamma delta T cells and/or NK T cells, as well as antibody or T-cell production in the subject to combat the infection. Methods to determine if an immune response has been elicited are known in the art and include, for example taking a suitable sample (blood, saliva or plasma) from a patient and assaying by ELISA cytokine levels, and whether antibodies against the pathogen or bacteria are present. In addition, non-invasive means such as a reduction in temperature of the subject can be used alone or in combination with clinical methods.

In one aspect, the bacterium is selected from *S. aureus, A. baumannii, K. pneumoniae, P. aeruginosa, E. coli, Enterobacter* spp., *Serratia, Stenotrophomonas*, and the fungus is selected from *Candida* spp.

The composition can be administered in any suitable dose as determined by the treating physician, health care professional or veterinarian. Non-limiting examples of suitable methods of administration comprise intramuscular, subcutaneous, or intravenous administration. The effective amount to be administered is from about 5 mcg/kg body weight to about 50 mcg/kg body weight, or alternatively 10 mcg/kg body weight to 50 mcg/kg body, or alternatively 20 mcg/kg body weight to about 50 mcg/kg body weight, or alternatively 10 mg/kg body weight to about 100 mcg/kg body weight, or alternatively from about 15 mcg/kg body weight to about 150 mcg/kg body weight, or alternatively from about 20 to mcg/kg body weight to about 200 mcg/kg body weight.

In one aspect, the composition is once, twice, or three times over the period of one to three months.

In another aspect, the method further comprises assaying the subject for a bacterial or fungal infection prior to administration of the composition using methods known in the art or as described herein.

The composition can be administered in any suitable dose as determined by the treating physician, health care professional or veterinarian. Non-limiting examples of suitable methods of administration comprise intramuscular, subcutaneous, or intravenous administration. The effective amount to be administered is from about 25 to mcg/kg body weight to about 200 mcg/kg body weight, or alternatively from about 50 mcg/kg body weight to about 175 mcg/kg body weight, or alternatively from about 75 to mcg/kg body weight to about 200 mcg/kg body weight, or from about 25 to mcg/kg body weight to about 100 mcg/kg body weight, or from about 25 to mcg/kg body weight to about 175 mcg/kg body weight, or from about 25 to mcg/kg body weight to about 150 mcg/kg body weight, or from about 75 to mcg/kg body weight to about 200 mcg/kg body weight, or from about 75 to mcg/kg body weight to about 150 mcg/kg body weight, or from about 25 to mcg/kg body weight to about 150 mcg/kg body weight, or from about 50 to mcg/kg body weight to about 125 mcg/kg body weight, or from about 50 to mcg/kg body weight to about 100 mcg/kg body weight, or alternatively about 25 mcg/kg body weight, or alternatively about 75 mcg/kg body weight, or alternatively about 100 mcg/kg body weight, or alternatively about 125 mcg/kg body weight, or alternatively about 150 mcg/kg body weight, or alternatively about 175 mcg/kg body weight, or alternatively about 200 mcg/kg body weight.

The methods also can be used to treat or prevent a disorder caused by a bacterial or fungal infection in a subject in need thereof, the method comprising administering an effective amount of the composition as described above. The subject to be treated is any animal or human patient at risk of or has developed infection from a bacterial (gram-positive or gram-negative bacteria) or fungus. Methods to determine if a subject has been treated include, for example taking a suitable sample (blood, saliva or plasma) from a patient and assaying by ELISA cytokine levels, and whether antibodies against the pathogen or bacteria are present. In addition, non-invasive means such as a reduction in temperature of the subject can be used alone or in combination with clinical methods. In addition, depending on the disease being treated, a reduction of clinical or symptoms of the disease is an indication of effective treatment.

In one aspect, the bacterium is selected from *S. aureus, A. baumannii, K. pneumoniae, P. aeruginosa, E. coli, Enterobacter* spp., *Serratia, Stenotrophomonas*, and the fungus is selected from *Candida* spp.

The composition can be administered in any suitable dose as determined by the treating physician, health care professional or veterinarian. Non-limiting examples of suitable methods of administration comprise intramuscular, subcutaneous, or intravenous administration. The effective amount to be administered is from about 25 to mcg/kg body weight to about 200 mcg/kg body weight, or alternatively from about 50 mcg/kg body weight to about 175 mcg/kg body weight, or alternatively from about 75 to mcg/kg body weight to about 200 mcg/kg body weight, or from about 25 to mcg/kg body weight to about 100 mcg/kg body weight, or from about 25 to mcg/kg body weight to about 175 mcg/kg body weight, or from about 25 to mcg/kg body weight to about 150 mcg/kg body weight, or from about 75 to mcg/kg body weight to about 200 mcg/kg body weight, or from about 75 to mcg/kg body weight to about 150 mcg/kg body weight, or from about 25 to mcg/kg body weight to about 150 mcg/kg body weight, or from about 50 to mcg/kg body weight to about 125 mcg/kg body weight, or from about 50 to mcg/kg body weight to about 100 mcg/kg body weight, or alternatively about 25 mcg/kg body weight, or alternatively about 75 mcg/kg body weight, or alternatively about 100 mcg/kg body weight, or alternatively about 125 mcg/kg body weight, or alternatively about 150 mcg/kg body weight, or alternatively about 175 mcg/kg body weight, or alternatively about 200 mcg/kg body weight.

In one aspect, the composition is once, twice, or three times over the period of one to three months. In one aspect, the immunization is boosted at from about 14 to about 28 days, post-immunization, or from at from about 16 to about 26 days, post-immunization, or at from about 18 to about 24 days, post-immunization, or from about 20 to about 26 days, post-immunization, or from about 22 to about 23 days post-immunization, or from at about 3 weeks post-immunization.

In another aspect, the method further comprises assaying the subject for a bacterial or fungal infection prior to administration of the composition using methods known in the art or as described herein.

The composition can be administered in any suitable dose as determined by the treating physician, health care professional or veterinarian. Non-limiting examples of suitable methods of administration comprise intramuscular, subcutaneous, or intravenous administration. The effective amount to be administered is from about 5 mcg/kg body weight to about 50 mcg/kg body weight, or alternatively 10 mcg/kg body weight to 50 mcg/kg body, or alternatively 20 mcg/kg body weight to about 50 mcg/kg body weight, or alternatively 10 mg/kg body weight to about 100 mcg/kg body weight, or alternatively from about 15 mcg/kg body weight to about 150 mcg/kg body weight, or alternatively from about 20 to mcg/kg body weight to about 200 mcg/kg body weight.

Kits

Also provided herein is a kit comprising the compositions or formulations as described herein and instructions for use.

Drug Screening Assay

Also provided herein is a method to identify an compound or agent that provides a benefit selected from one or more of: enhances immunity against a bacterial or fungal microbial infection or treats a bacterial or fungal infection or a disease related to a bacterial or fungal microbial infection, the method comprising admixing the compound or agent with the composition as described herein and administering the admixed composition to a non-human subject infected with a bacterial or fungal microorganism and assaying for post-administration infection or survival, wherein the compound or agent that enhances the activity of the composition as described herein is a compound or an agent that provides the benefit. Methods to determine if an immune response has been elicited are known in the art and include, for example taking a suitable sample (blood, saliva or plasma) from a patient and assaying by ELISA cytokine levels, and whether antibodies against the pathogen or bacteria are present. In addition, non-invasive means such as a reduction in temperature of the subject can be used alone or in combination with clinical methods. Methods to determine if a subject has been treated include, for example taking a suitable sample (blood, saliva or plasma) from a patient and assaying by ELISA whether antibodies against the pathogen or bacteria are present. In addition, non-invasive means such as a reduction in temperature of the subject can be used alone or in combination with clinical methods. In addition, depending on the disease being treated, a reduction of clinical or symptoms of the disease is an indication of effective treatment.

Materials and Methods

Preparation of Compositions

To prepare the compositions, the preferred amount of aluminum hydroxide is suspended in saline solution to a concentration in a range from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or altern 0.1 mg/ml to about 1 mg/ml, or alternatively from about 0.2 mg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

The MPL is suspended in pharmaceutically acceptable carriers such as PBS, to a concentration in a range from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or altern 0.1 mg/ml to about 1 mg/ml, or alternatively from about 0.2 mg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

The MP and WGP are then combined in any appropriate combination and it is not intended that the ratios of each component be identical, although they can be combined in a 1:1 ratio. Alternatively the MP is combined with the WGP in a ratio of about 0.1:1; about 0.2:1; about 0.3:1; about 0.4:1; about 0.5:1; about 0.6:1; or about 0.7:1; or about 0.8:1; or about 0.9:1; or about 1:1. Alternatively the WGP and MPL can combined with the WGP in a ratio of about 0.1:1; about 0.2:1; about 0.3:1; about 0.4:1; about 0.5:1; about 0.6:1; or about 0.7:1; or about 0.8:1; or about 0.9:1; or about 1:1.

After this combination of the MPL and WGP, the combination is further admixed with aluminum hydroxide at about 1:5, or alternatively about 1:6, or alternatively about 1:7, or alternatively about 1:8, or alternatively about 1:9, or alternatively about 1:10, or alternatively about 1:11, or alternatively about 1:12 or alternatively about 1:13, or alternatively about 1:14, or alternatively about 1:15, or alternatively about 1:16, or alternatively about 1:17, or alternatively about 1:18, or alternatively about 1:19 or alternatively about 1:20 ratio.

In some aspect, mannan is dissolved in saline to provide a concentration of from about 0.1 mg/ml to about 10 mg/ml, or alternatively from about 0.5 mg/ml to about 10 mg/ml, or alternatively from about 1.0 mg/ml to about 10 mg/ml, or alternatively from about 0.1 mg/ml to about 9 mg/ml, or alternatively from about 0.1 mg/ml to about 7 mg/ml, or alternatively from about 0.1 mg/ml to about 5 mg/ml0, or alternatively from about 0.1 mg/ml to about 3 mg/ml, or alternatively from about 0.1 mg/ml to about 2 mg/ml, or alternatively from about 0.1 mg/ml to about 1 mg/ml, or alternatively from about 0.2 mg/ml to about 8 mg/ml, or alternatively from about 0.1 mg/ml to about 5 mg/ml, or alternatively from about 0.1 mg/ml to about 3 mg/ml, or alternatively from about 0.5 mg/ml to about 3 mg/ml, or alternatively from about 0.5 mg/ml to about 2 mg/ml, or about 0.5 mg/ml, or about 1.0 mg/ml, or about 1.5 mg/ml, or about or about 0.5 mg/ml, or about 1.0 mg/ml, or about 1.5 mg/ml, or about 2.0 mg/ml, or about 3.0 mg/ml, or about 3.5 mg/ml, or about 4.0 mg/ml, or about 4.5 mg/ml, or about 5 mg/ml, or about 5.5 mg/ml, or about 6.0 mg/ml, or about 6.5 mg/ml, or about 7.0 mg/ml, or about 7.5 mg/ml, or about 8.0 mg/ml, or about 8.5 mg/ml, or about 9.0 mg/ml, or about 9.5 mg/ml or about 10 mg/ml.

Alternatively, the aluminum hydroxide and MPL are sourced from a commercial vendor such GlaxoSmithKline (GSK) and combined with mannan and WGP in amounts as noted above.

The compositions can be formulated for in vivo administration (in one or more doses) to administer from about 5 mcg/kg body weight to about 50 mcg/kg body weight, or alternatively 10 mcg/kg body weight to 50 mcg/kg body, or alternatively 20 mcg/kg body weight to about 50 mcg/kg body weight, or alternatively 10 mg/kg body weight to about 100 mcg/kg body weight, or alternatively from about 15 mcg/kg body weight to about 150 mcg/kg body weight, or alternatively from about 20 to mcg/kg body weight to about 200 mcg/kg body weight.

Experiment No. 1

Vaccine Efforts Targeting S. aureus.

Figure 1A:
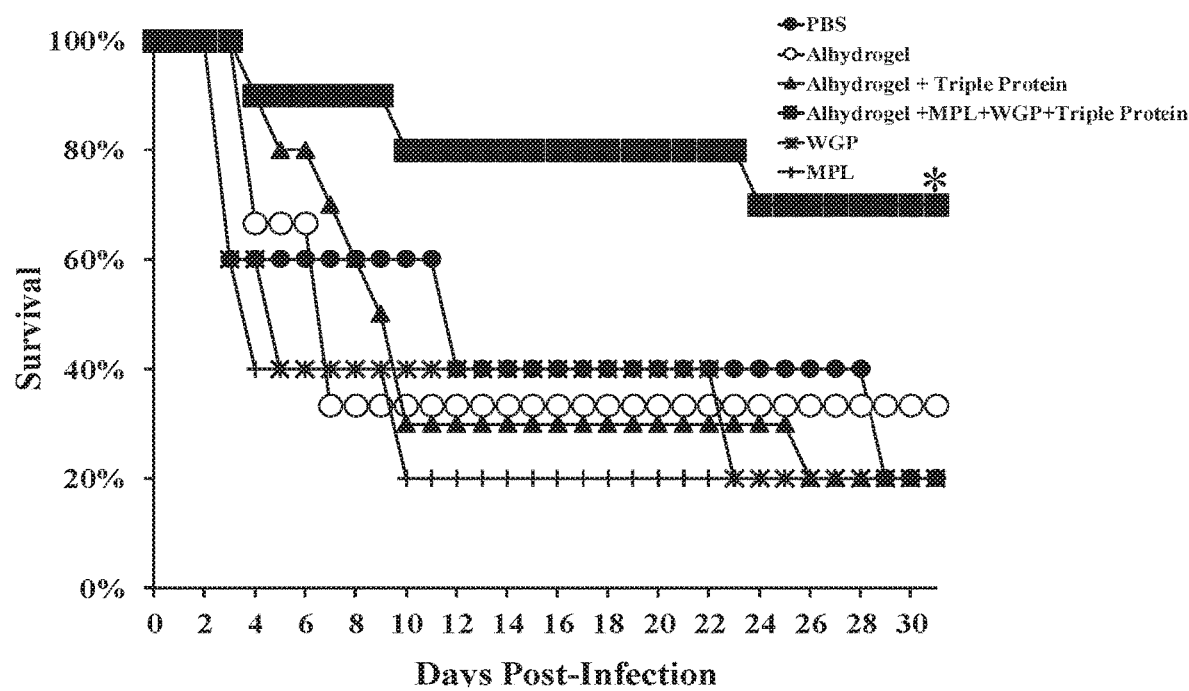
FIGS. 1A and B results of various adjuvants against *S. aureus* infection.
Figure 1B:
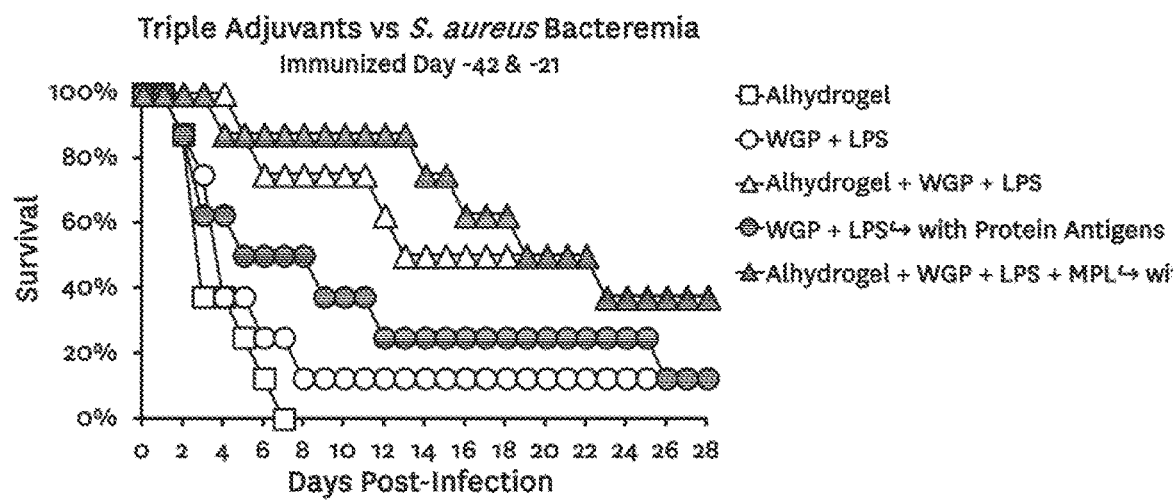
FIG. 1B compares adjuvants with versus without *S. aureaus* protein antigens, mice immunized with adjuvants only survived as well as mice with adjuvants and protein antigens.

Applicants studied 14 candidate proteins, which were systematically screened for efficacy against S. aureus bacteremia in combination with aluminum hydroxide adjuvant (Al(OH)$_3$). However, no combination of proteins administered with Al(OH)$_3$ adjuvant was found to improve survival in mice infected IV with S. aureus. As a result, Applicants therefore tried substituting the adjuvant to improve efficacy. By combining 3 adjuvants, including (Al(OH)$_3$, monophosphoryl lipid (MPL), and whole glucan particles (WGP)) with the 3 staphylococcal proteins (alpha toxin, ABC transporter protein, and ABC transporter protein 2), administering the regimen with a boost 3 weeks after the primary immunization, and infecting the mice two weeks later, Applicants show significant improvement in survival compared to PBS (saline) alone (FIG. 1A).

Triple adjuvants were also assayed against S. aureus Bacteremia. Antibiotic-resistant clinical isolates of S. aureus (LAC) and A. baumannii (HUMC1), with $10^7$ to $10^8$ CFUs injected via the tail vein. Subcutaneous injection of 200 μl in scruff of neck (Alhydrogel, 1.3% depot formation, NALP3 inflammasome activator; MPL (monophosphory lipid A), 10 μg, detoxified LPS; WGP (whole glucan particle), 100 μg, fungal surface carbohydrates.

Figure 2:
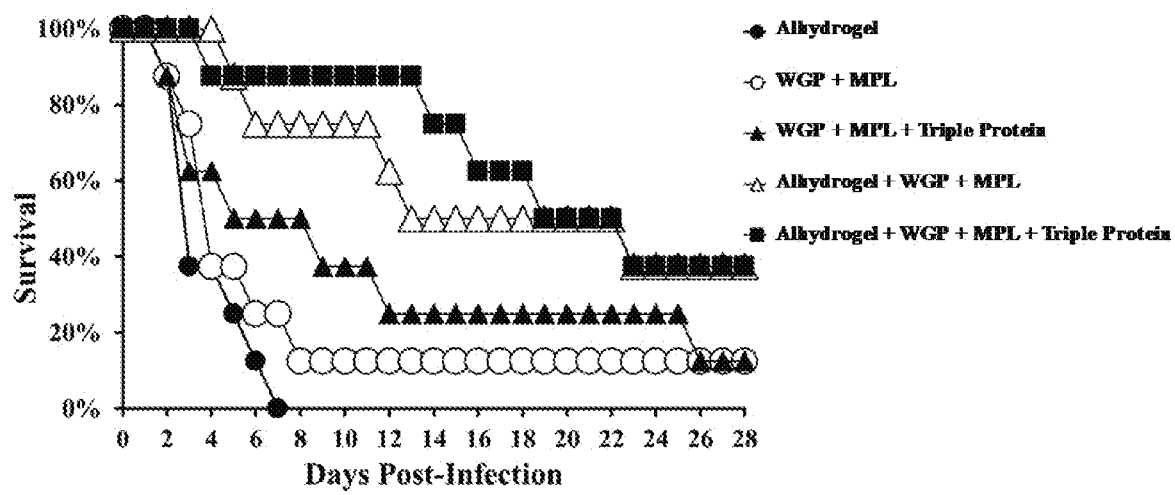
FIG. 2 shows that BALB/c mic e were vaccinated with various combinations of adjuvant and proteins and infected IV via the tail-vein with *S. aureus* LAC (community-acquired MRSA strain). Mice immunized with triple adjuvant (Alhydrogel+WGP+MPL) had the same improvement in survival as mice immunized with triple adjuvant and triple protein. Thus, adjuvant was mediating the protection, rather than protein. N=8 mice per group. *$p<0.05$ vs. control.

In a repeat experiment, when triple adjuvant+protein was compared to triple adjuvant alone, the efficacy did not differ, indicating that the primary driver of efficacy was the adjuvants, not the protein (FIG. 2). Furthermore, dual adjuvant was not effective, indicating that all 3 components of the adjuvant are necessary for efficacy (FIG. 2). Thus, this combination of adjuvants is non-obvious, as each component alone does not mediate protection. Finally, Applicants emphasize that this triple adjuvant regimen was administered on day 1 and 22, and infection was on day 36, indicating that the regimen retained efficacy for at least 14 days after last dose.

Figure 3:
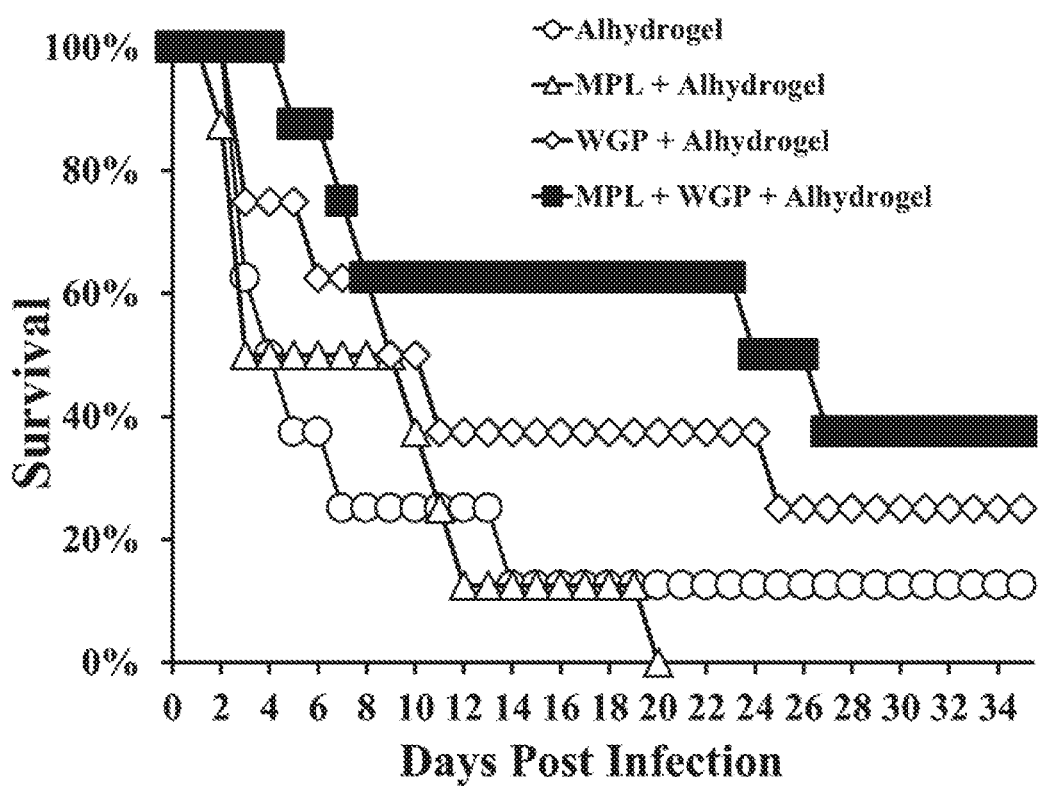
FIG. 3 shows that when BALB/c mic e were vaccinated with various combinations of adjuvants and infected IV via the tail-vein with *S. aureus* LAC. Triple adjuvant was the most effective approach. N=8 mice per group. *$p<0.05$ vs. control.

Applicants repeated the experiment to determine if the other dual adjuvant combinations had efficacy. Triple adjuvant was once again highly protective (FIG. 3). Dual adjuvants with aluminum hydroxide plus monophosphoryl lipid (MPL) was not effective (FIG. 3). Some efficacy was seen with dual adjuvant with aluminum hydroxide and whole glucan particles (WGP), but the efficacy was optimal with triple adjuvants (FIG. 3). In combination with data from FIG. 2 showing no efficacy of dual adjuvant with WGP plus MPL, the efficacy of triple therapy is clearly non-obvious.

Figure 4:
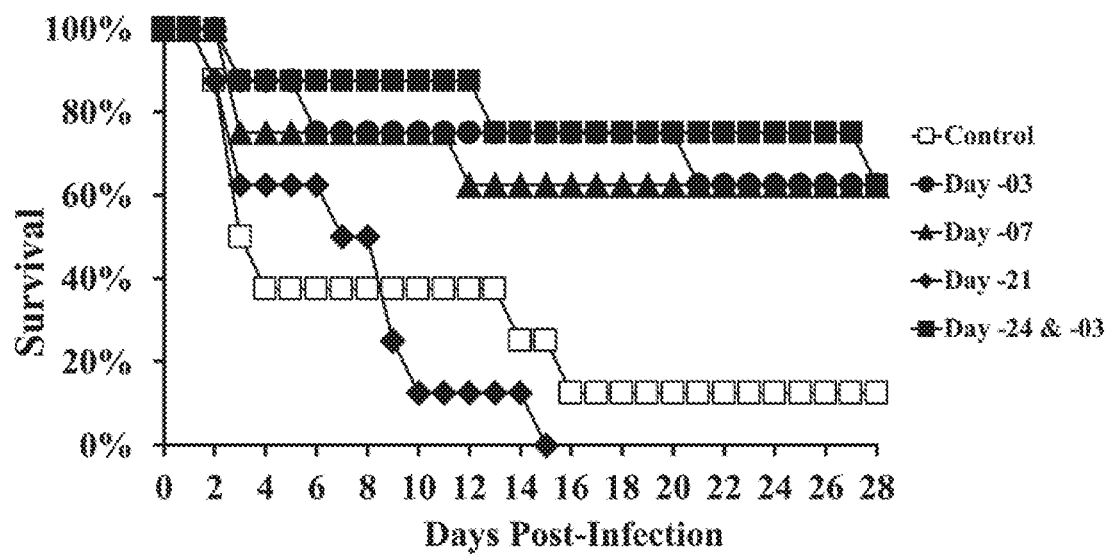
FIG. 4 shows that triple adjuvant regimen has durable protection for ≥7 days. BALB/c mice were vaccinated with triple adjuvants and infected IV via the tail-vein with *S. aureus* LAC 3, 7, or 21 days later. Some mice were boosted at 3 weeks and infected 3 days later. N=8 mice per group. *$p<0.05$ vs. control.

Finally, Applicants sought to determine the potential duration of protection against S. aureus mediated by triple adjuvants. Mice were immunized with a single dose of triple adjuvant and infected at either 3, 7, or 21 days later. Another group was immunized with triple adjuvant and boosted at 3 weeks, and the infected 3 days later. Protection persisted for 3 and 7 days (FIG. 4).

Applicants began to develop a novel concept, that adjuvants alone might be able to provide short- to intermediate-term protection against HAI pathogens in patients at acute risk in the hospital. Only several weeks of protection would be required, spanning the period of hospitalization, and adjuvants could mediate such protection without a protein to induce long-term immunological memory.

Experiment No. 2.

Adjuvant Efficacy Against Gram-Negative Pathogens.

Aluminum has been used in vaccines since the 1930s and generic Al(OH)$_3$ is an FDA-approved adjuvant that is included in the hepatitis A, hepatitis B, TDaP, Hib, and HPV vaccine formulations. (7-9) MPL is a detoxified lipopolysaccharide (endotoxin) product that activates TLR4 and is included in the FDA-approved Fendrix hepatitis B virus (HBV) and HPV vaccine (Cervarix). (9) Thus, these two components of the adjuvant mixture are already used in FDA-approved vaccines. The WGP adjuvant signals through Dectin-1 on macrophages and dendritic cells. (10-12) Vaccines including glucan are not yet FDA-approved, although vaccines including glucan have already entered clinical trials. (11, 12) As such, all of these adjuvants have been individually studied in patients and could therefore be rapidly translated into a prophylactic regimen for HAIs.

Figure 5:
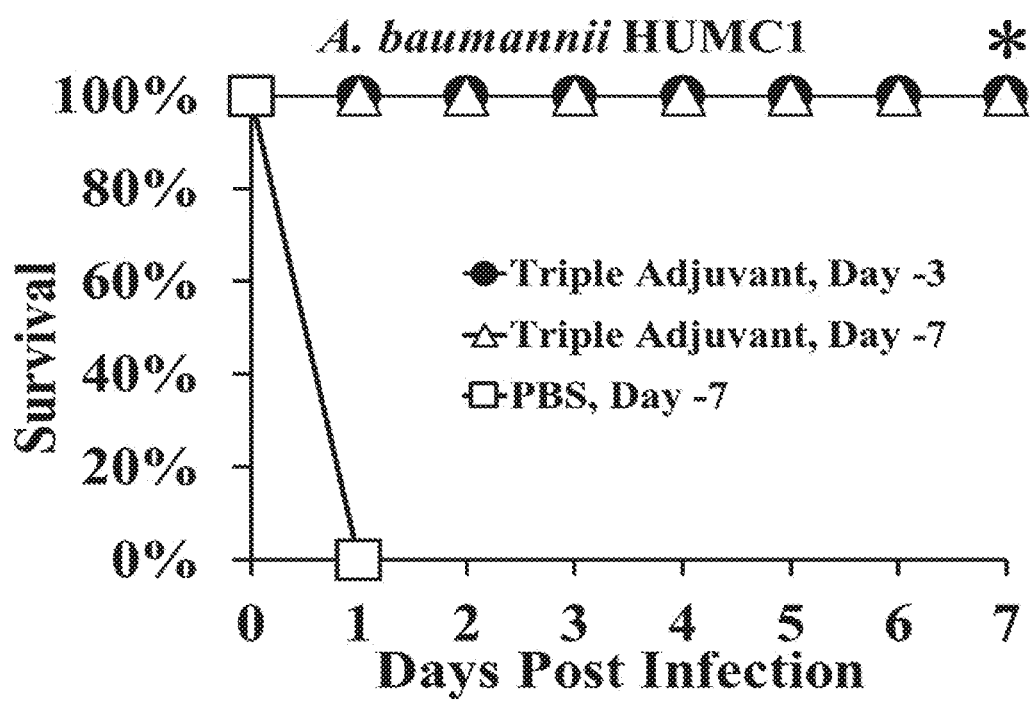
FIG. 5 shows that C3HeB/Fe mice were infected with *A. baumannii* 3 or 7 days after being vaccinated with a single dose of the optimal triple adjuvant regimen (Al(OH)$_3$+ MPL+WGP). All mice receiving the triple adjuvant survived whereas all control mice died. N=6 mice per group. *$p<0.05$ vs. control.

Following on the efficacy seen against S. aureus bacteremia, Applicants sought to determine if this novel adjuvant mixture could also mediate protection against Gram-negative pathogens. Mice were immunized as above with a single SC dose of either the triple adjuvant regimen or saline placebo. Three or 7 days later mice were infected IV with A. baumannii HUMC1 (a hyper-virulent, carbapenem-resistant, clinical blood and lung isolate) or K. pneumoniae KP3 (a hyper-virulent, clinical blood isolate). All mice immunized with triple adjuvant survived A. baumannii infection whereas all control mice died (FIG. 5).

Figure 6:
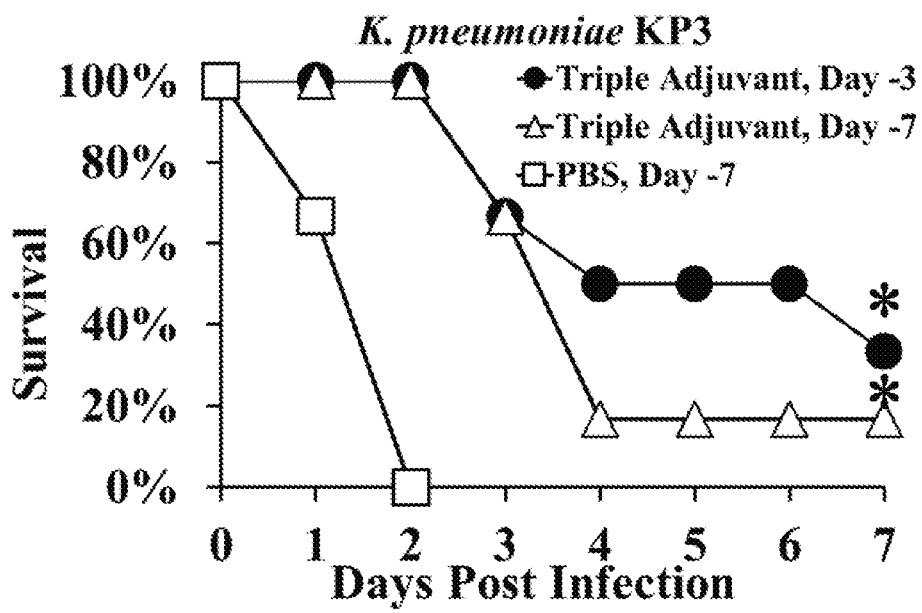
FIG. 6 shows that when C3HeB/Fe mice were infected with *K. pneumoniae* 3 or 7 days after being vaccinated with a single dose of the optimal triple adjuvant regimen (Al(OH)$_3$+MPL+WGP). Mice receiving the triple adjuvant regimen had significantly improved survival compared to control mice. N=6 mice per group. *$p<0.05$ vs. control.

For mice infected with K. pneumoniae, immunization with a single dose of triple adjuvant also statistically significantly improved survival compared to control (FIG. 6).

Figure 7:
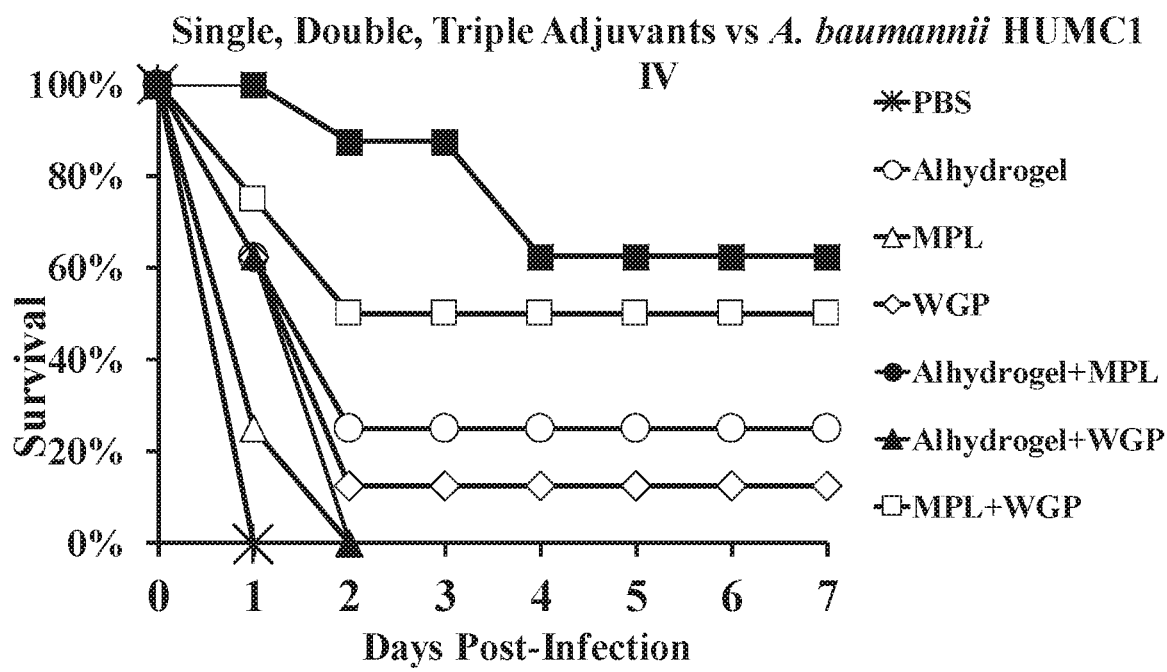
FIG. 7 shows that when C3HeB/Fe mice were infected with *A. baumannii* 3 or 7 days after being vaccinated with single, dual, or triple adjuvant. Mice receiving the triple adjuvant regimen had significantly improved survival compared to control mice. N=8 mice per group. *$p<0.05$ vs. control.

Finally, to begin establishing the requisite composition of the adjuvants to mediate protection, mice were immunized with a single dose of the various dual adjuvant combinations versus triple adjuvant, or saline control. Mice were infected IV via the tail-vein with A. baumannii HUMC1 3 days after immunization. Mice immunized with the triple adjuvant combination had the best survival compared to all other groups (FIG. 7). Furthermore, dual aluminum hydroxide plus WGP or MPL had no efficacy (FIG. 7). Surprisingly aluminum hydroxide alone mediated statistically significantly improved survival vs. A. baumannii, while it had mediated no benefit at all vs. S. aureus, and adding WGP or MPL to it abrogated its efficacy. Similarly, WGP plus MPL mediated some efficacy vs. A. baumannii whereas it had mediated no efficacy vs. S. aureus. But triple therapy was superior to WGP plus MPL and aluminum hydroxide alone. Collectively these results underscore the complexity of combining multiple adjuvants and testing against multiple organisms, and the non-obvious nature of the fact that triple combination adjuvants mediate protection against Gram positive and negative pathogens, when single and dual combinations do not reliably do so.

Experiment No. 3

The Role of Mannan as a Potential Fourth Adjuvant.

Figure 8:
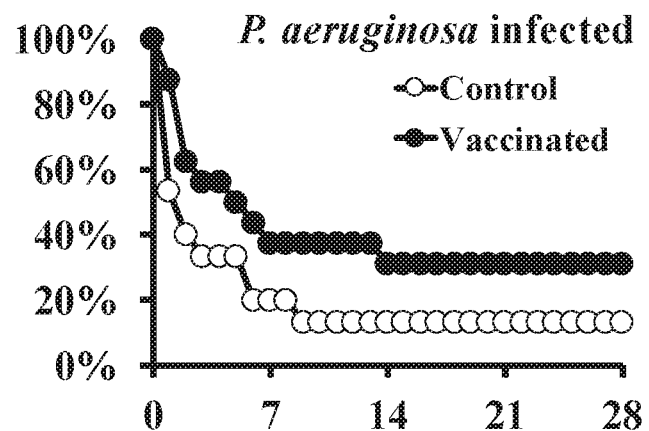
FIG. 8 shows that when mice were vaccinated and boosted with rAsl3p-N+Al(OH)$_3$ or Al(OH)$_3$ alone (control) and infected IV via the tail-vein with *P. aeruginosa* PA01. N=15 control mice and 16 vaccinated mice from 2 experiments. $p=0.07$ by Log Rank test.
Figure 9:
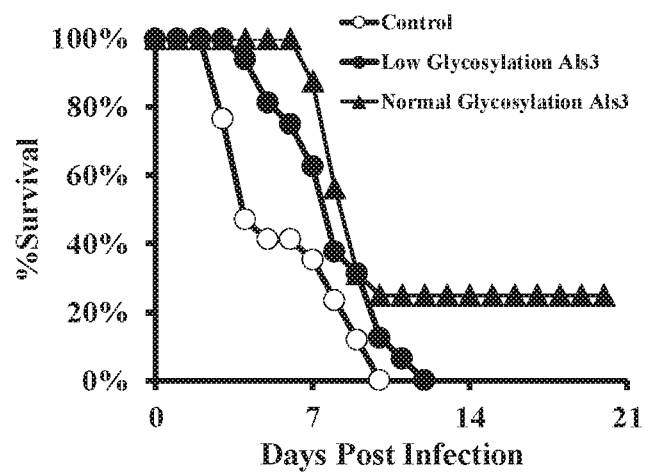
FIG. 9 shows that when mice were vaccinated and boosted with Al(OH)$_3$ plus Als3p with either normal or decreased glycosylation, or Al(OH)$_3$ alone as a control. N=17 control mice, and 16 mice each for both vaccine groups. Mice were infected with *C. albicans* SC5314. $p=0.002$ by Log-Rank test for normal glycosylation vs. control; >0.2 for low glycosylation vs. control.

Previous researchers have investigated the mechanism of vaccine-mediated protection of the N terminus of the recombinant agglutinin-like sequence 1 and 3 (rAls1p-N and rAls3p-N) vaccines. (13-38) For example, one study was conducted infected mice with P. aeruginosa as a negative control (aiming to demonstrate specificity of the protein for S. aureus). Surprisingly, for a total of 16 mice per group from 2 experiments, there was a substantial trend to improved survival with mice vaccinated with rAls3p-N and infected with *P. aeruginosa* (p=0.07, FIG. 8). These results suggested that indeed at least some of the efficacy of rAls3p-N could be attributed to general immune stimulation, as there is no homology of rAls3p-N to the *P. aeruginosa* proteome.

Contemporaneously, other groups published studies demonstrating that fungal mannans (a type of sugar) had potent Th1/Th17 activation properties and could markedly stimulate both innate and adaptive immune responses. For example, Lam et al. (39) produced recombinant ovalbumin that either was or was not mannosylated by yeast during production. Yeast-mannosylated ovalbumin non-specifically induced significantly greater T cell proliferation than did non-glycosylated ovalbumin produced in *E. coli*. Furthermore, the stimulatory effect was attributable to O-mannosylation rather than N-mannosylation. Chemical deglycosylation abrogated the stimulatory effect of the mannosylated protein, as did mixing of the mannosylated protein with free *S. cerevisiae* mannans during lymphocyte co-culture, confirming that the yeast mannosylation was responsible for the immunological effect. A similar immunostimulatory effect of mannosylated proteins was seen on CD8+ T cell function. (40) Not only was CD8+ T cell proliferation enhanced, secretion of pro-inflammatory cytokines, such as TNF and IL-12, was also markedly enhanced by mannosylation of the target antigen. Most recently, O-mannosylated glycolipids have been shown to activate invariant NKT cells which protect against lethal pneumococcal infection. (41)

Thus, Applicants began to suspect that the O-glycosylation of Als3 might be responsible for its efficacy. Applicants were able to isolate a mutant clone of *S. cerevisiae* that produced Als3p with a decreased mannan content (<80% mannan vs. >90% for the original clone).

Figure 10:
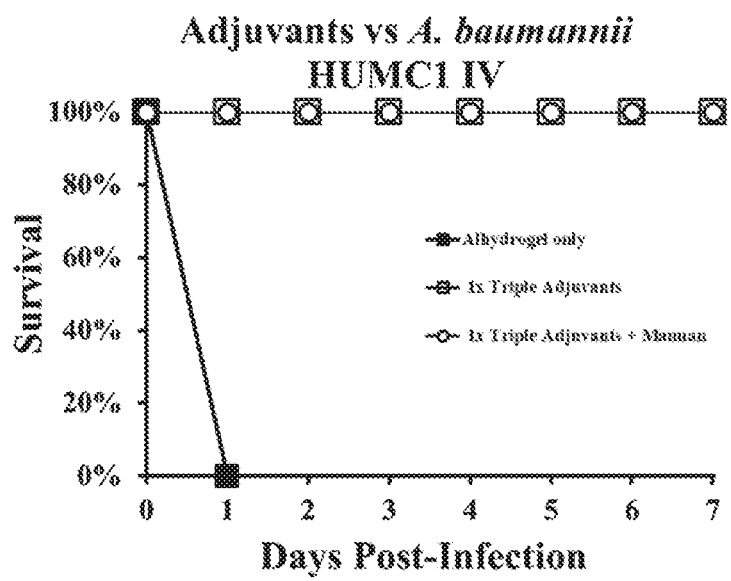
FIG. 10. Mice were administered triple adjuvant, quadruple adjuvant (including mannan), or PBS alone. Mice were challenged with *A. baumannii* HUMC1 ($2\times10^7$ CFUs).

Applicants determined the impact of adding mannan on top of the triple adjuvant mixture (A10H3+MPL+WGP). Efficacy of the quadruple regimen was compared to the triple adjuvant regimen in protecting mice against *A. baumannii* HUMC1 infection. Mice immunized with quadruple adjuvant (including mannan) appeared clinically improved at days 2-4 post-infection compared to mice immunized with triple adjuvant (no ruffled fur, normal activity level, and no weight loss in the quadruple group vs. ruffled fur with diminished activity for mice in the triple adjuvant group). However, all mice in both immunized groups survived, so it was not possible to distinguish efficacy based on a time to death outcome between the triple and quadruple adjuvant regimens, because triple adjuvant alone was so effective (FIG. 10).

Figure 11:
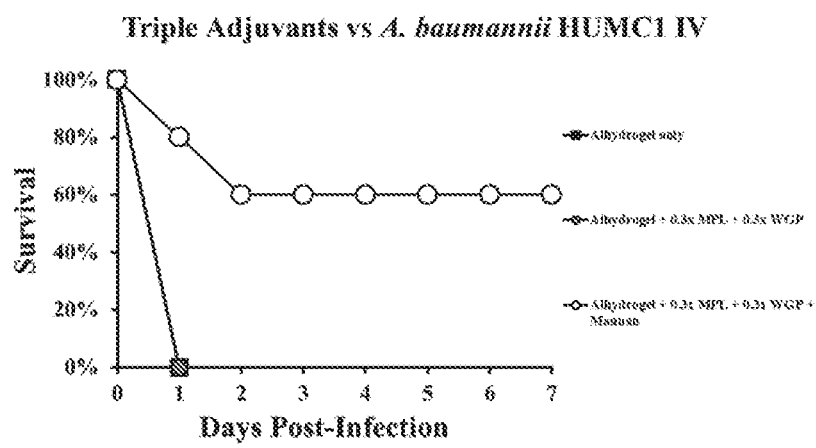
FIG. 11. Mice were administered triple adjuvant, quadruple adjuvant (including mannan), or PBS alone. The triple adjuvant group were given Al(OH)$_3$ (1.3%)+MPL (30

The experiment was repeated but the dose of MPL and WGP was reduced to ⅓ that present normally, and the mixture of administration with aluminum was altered to decrease the uptake of the triple adjuvant (package insert for aluminum hydroxide recommends 5 minutes of agitation with the material to be bound to the adjuvant. This was done for 10 seconds to decrease MPL/WGP retention on the aluminum). The purpose was to decrease the efficacy of the triple regimen to determine if adding the mannan as a fourth adjuvant would improve efficacy. Indeed, all suboptimal triple adjuvant immunized mice died, while the quadruple immunized mice had marked improvements in survival (FIG. 11).

Dosing schedules were evaluated to determine if lower doses might be effective. In the first experiment, mice were infected with *S. aureus* LAC (MRSA). The inoculum of the infection ($8.4 \times 10^7$) was 33% above intended. Dosing down 10-fold with the triple adjuvant regimen retained protection similar to the higher doses of adjuvant (FIG. 12), indicating potential for lower dosing, which will make cost of goods more financially attractive for clinical development.

Experiment No. 4 rAls3p-N with Diminished Mannan Content Offered Significantly Less Protection than the Normal Clone.

Without being bound by theory, this disclosure provides that mannan is a fourth adjuvant that provides broad spectrum protection against healthcare associated pathogens, including *P. aeruginosa* and *C. albicans*.

Experiment No. 5

Different Immunization Schedules.

Figure 1C:
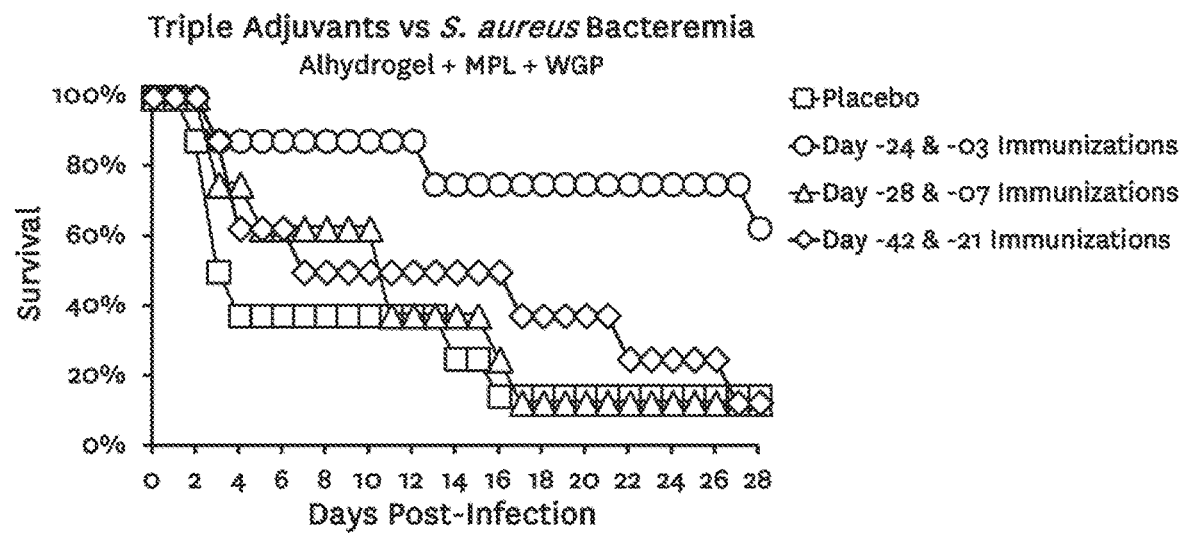
FIGS. 1C and 1D show that different immunization schedules improve survival.
Figure 1D:
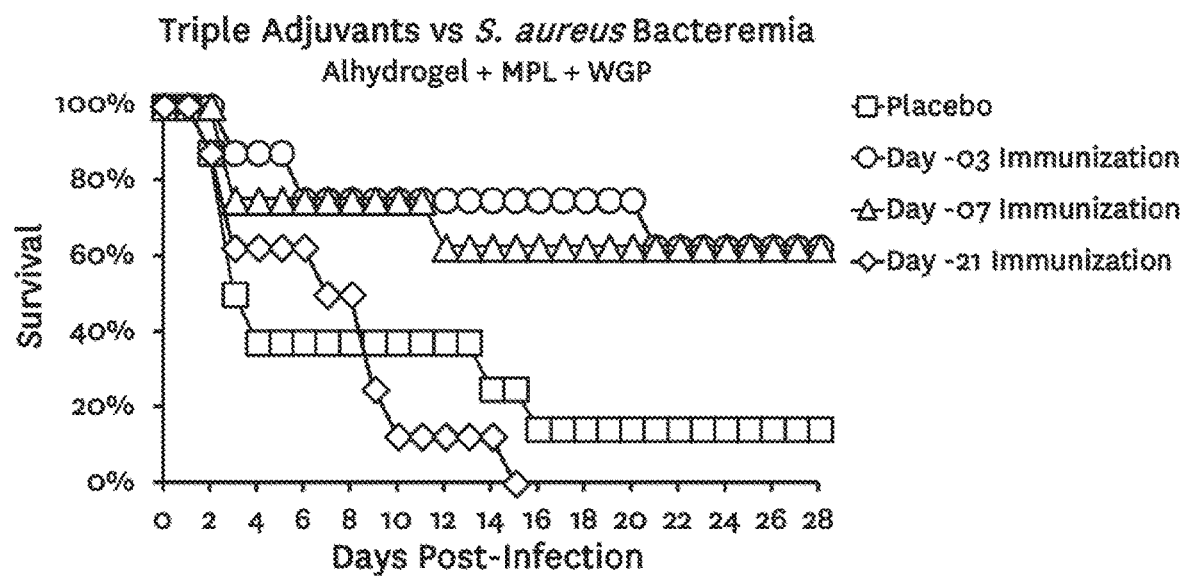

As shown in FIGS. 1C and 1D, Applicants show the different immunization schedules improve survival. FIG. 1C shows that maintaining 3 weeks between prime and boost, but with various delay between boost and infection. FIG. 1D shows that singe immunization (i.e., no booster) with variable delay between immunizations and infection.

EQUIVALENTS

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

REFERENCES

1. Marchetti A, Rossiter R. Economic burden of healthcare-associated infection in US acute care hospitals: societal perspective. J Med Econ 2013; 16:1399-404.
2. Leading Causes of Death: Number of deaths for leading causes of death. US Centers for Disease Control and Prevention, 2007. Aug. 13, 2010, at cdc.gov/nchs/fastats/lcod.htm.)
3. Infectious Diseases Society of A. White paper: recommendations on the conduct of superiority and organism-specific clinical trials of antibacterial agents for the treatment of infections caused by drug-resistant bacterial pathogens. Clin Infect Dis 2012; 55:1031-46.
4. Spellberg B, Bartlett J G, Gilbert D N. The future of antibiotics and resistance. N Engl J Med 2013; 368:299-302.
5. Bartlett J G, Gilbert D, Spellberg B. Seven Ways to Preserve the Miracle of Antibiotics. Clin Infect Dis 2013; 56:1445-50.
6. Wenzel R P, Edmond M B. Infection control: the case for horizontal rather than vertical interventional programs. International journal of infectious diseases: IJID: official publication of the International Society for Infectious Diseases 2010; 14 Suppl 4:S3-5.
7. Baylor N W, Egan W, Richman P. Aluminum salts in vaccines—US perspective. Vaccine 2002; 20 Suppl 3:S18-23.
8. Vaccine Excipient & Media Summary. US CDC; 2017.
9. Rappuoli R, Mandl C W, Black S, De Gregorio E. Vaccines for the twenty-first century society. Nature reviews Immunology 2011; 11:865-72.
10. Goodridge H S, Reyes C N, Becker C A, et al. Activation of the innate immune receptor Dectin-1 upon formation of a 'phagocytic synapse'. Nature 2011; 472:471-5.
11. Levitz S M, Huang H, Ostroff G R, Specht C A. Exploiting fungal cell wall components in vaccines. Semin Immunopathol 2015; 37:199-207.
12. Li P, Wang F. Polysaccharides: Candidates of promising vaccine adjuvants. Drug Discov Ther 2015; 9:88-93.
13. Fu Y, Filler S G, Spellberg B J, et al. Cloning and characterization of CAD1/AAF1, a gene from *Candida albicans* that induces adherence to endothelial cells after expression in *Saccharomyces cerevisiae*. Infection and immunity 1998; 66:2078-84.
14. Fu Y, Ibrahim A S, Sheppard D C, et al. *Candida albicans* Als1p: an adhesin that is a downstream effector of the EFG1 filamentation pathway. Molec Microbiol 2002; 44:61-72.
15. Fu Y, Rieg G, Fonzi W A, Belanger P H, Edwards J E, Jr., Filler S G. Expression of the *Candida albicans* gene ALS1 in *Saccharomyces cerevisiae* induces adherence to endothelial and epithelial cells. Infection and immunity 1998; 66:1783-6.
16. Ibrahim A S, Filler S G, Sanglard D, Edwards J E, Jr., Hube B. Secreted aspartyl proteinases and interactions of *Candida albicans* with human endothelial cells. Infection and immunity 1998; 66:3003-5.
17. Rieg G, Fu Y, Ibrahim A S, Zhou X, Filler S G, Edwards J E, Jr. Unanticipated heterogeneity in growth rate and virulence among *Candida albicans* AAF1 null mutants. Infection and immunity 1999; 67:3193-8.
18. Orozco A S, Zhou X, Filler S G. Mechanisms of the proinflammatory response of endothelial cells to *Candida albicans* infection. Infection and immunity 2000; 68:1134-41.
19. Tsuchimori N, Sharkey L L, Fonzi W A, French S W, Edwards J E, Jr., Filler S G. Reduced virulence of HWP1-deficient mutants of *Candida albicans* and their interactions with host cells. Infection and immunity 2000; 68:1997-2002.
20. Phan Q T, Belanger P H, Filler S G. Role of hyphal formation in interactions of *Candida albicans* with endothelial cells. Infection and immunity 2000; 68:3485-90.
21. Davis D, Edwards J E, Jr., Mitchell A P, Ibrahim A S. *Candida albicans* RIM101 pH response pathway is required for host-pathogen interactions. Infection and immunity 2000; 68:5953-9.
22. Clemons K V, Calich V L, Burger E, et al. Pathogenesis I: interactions of host cells and fungi. Medical mycology: official publication of the International Society for Human and Animal Mycology 2000; 38 Suppl 1:99-111.
23. Cannom R R, French S W, Johnston D, Edwards Jr J E, Filler S G. *Candida albicans* stimulates local expression of leukocyte adhesion molecules and cytokines in vivo. J Infect Dis 2002; 186:389-96.
24. Kamai Y, Kubota M, Hosokawa T, Fukuoka T, Filler S G. Contribution of *Candida albicans* ALS1 to the pathogenesis of experimental oropharyngeal candidiasis. Infection and immunity 2002; 70:5256-8.
25. Belanger P H, Johnston D A, Fratti R A, Zhang M, Filler S G. Endocytosis of *Candida albicans* by vascular endothelial cells is associated with tyrosine phosphorylation of specific host cell proteins. Cellular microbiology 2002; 4:805-12.
26. Spellberg B, Edwards J E, Jr. Type 1/Type 2 immunity in infectious diseases. Clin Infect Dis 2001; 32:76-102.
27. Spellberg B J, Johnston D, Phan Q T, et al. Parenchymal organ, and not splenic, immunity correlates with host survival during disseminated candidiasis. Infection and immunity 2003; 71:5756-64.
28. Sanchez A A, Johnston D A, Myers C, Edwards J E, Jr., Mitchell A P, Filler S G. Relationship between *Candida albicans* virulence during experimental hematogenously disseminated infection and endothelial cell damage in vitro. Infection and immunity 2004; 72:598-601.
29. Loza L, Fu Y, Ibrahim A S, Sheppard D C, Filler S G, Edwards J E, Jr. Functional analysis of the *Candida albicans* ALS1 gene product. Yeast 2004; 21:473-82.
30. VandenBerg A L, Ibrahim A S, Edwards J E, Jr., Toenjes K A, Johnson D I. Cdc42p GTPase regulates the budded-to-hyphal-form transition and expression of hypha-specific transcripts in *Candida albicans*. Eukaryot Cell 2004; 3:724-34.
31. Sheppard D C, Yeaman M R, Welch W H, et al. Functional and structural diversity in the Als protein family of *Candida albicans*. J Biol Chem 2004; 279: 30480-9.
32. Ibrahim A S, Spellberg B J, Avenissian V, Fu Y, Filler S G, Edwards J E, Jr. Vaccination with recombinant N-terminal domain of Als1p improves survival during murine disseminated candidiasis by enhancing cell-mediated, not humoral, immunity. Infection and immunity 2005; 73:999-1005.
33. Spellberg B J, Ibrahim A S, Avenissian V, et al. The anti-*Candida albicans* vaccine composed of the recombinant N terminus of Als1p reduces fungal burden and improves survival in both immunocompetent and immunocompromised mice. Infection and immunity 2005; 73:6191-3.
34. Spellberg B, Ibrahim A S, Edwards Jr J E, Filler S G. Mice with disseminated candidiasis die of progressive sepsis. J Infect Dis 2005; In press.
35. Toenjes K A, Munsee S M, Ibrahim A S, Jeffrey R, Edwards J E, Jr., Johnson D I. Small-molecule inhibitors of the budded-to-hyphal-form transition in the pathogenic yeast *Candida albicans*. Antimicrob Agents Chemother 2005; 49:963-72.
36. Phan Q T, Fratti R A, Prasadarao N V, Edwards J E, Jr., Filler S G. N-cadherin mediates endocytosis of *Candida albicans* by endothelial cells. J Biol Chem 2005; 280: 10455-61.
37. Spellberg B J, Ibrahim A S, Avanesian V, et al. Efficacy of the anti-*Candida* rAls3p-N or rAls1p-N vaccines against disseminated and mucosal candidiasis. J Infect Dis 2006; 194:256-60.
38. Ibrahim A S, Spellberg B J, Avanesian V, Fu Y, Edwards J E J. The anti-*Candida* rAls1p-N vaccine is broadly active against disseminated candidiasis. Infection and immunity 2006; 74:3039-41.
39. Lam J S, Mansour M K, Specht C A, Levitz S M. A model vaccine exploiting fungal mannosylation to increase antigen immunogenicity. Journal of immunology 2005; 175:7496-503.
40. Luong M, Lam J S, Chen J, Levitz S M. Effects of fungal N- and O-linked mannosylation on the immunogenicity of model vaccines. Vaccine 2007; 25:4340-4.
41. Shimamura M, Yamamura M, Nabeshima T, et al. Activation of invariant natural killer T cells stimulated with microbial alpha-mannosyl glycolipids. Sci Rep 2017; 7:9703.
42. Endo T. Structure, function and pathology of 0-mannosyl glycans. Glycoconj J 2004; 21:3-7.
43. Leitao E A, Bittencourt V C, Haido R M, et al. Beta-galactofuranose-containing 0-linked oligosaccharides present in the cell wall peptidogalactomannan of *Aspergillus fumigatus* contain immunodominant epitopes. Glycobiology 2003; 13:681-92.
44. Peter-Katalinic J. Methods in enzymology: O-glycosylation of proteins. Methods in enzymology 2005; 405: 139-71.

What is claimed is:

1. A composition consisting essentially of an effective amount of each of aluminum hydroxide, mono-phosphoryl lipid (MPL), and whole glucan particles (WGP) with the proviso that the composition does not comprise an antigen effective to induce an immune response against a fungus or a bacterium.

2. A composition consisting essentially of an effective amount of each of aluminum hydroxide, mono-phosphoryl lipid (MPL), whole glucan particles (WGP), and mannan with the proviso that the composition does not comprise an antigen effective to induce an immune response against a fungus or a bacterium.

3. The composition of claim 1, wherein the effective amount of the aluminum hydroxide is from 0.1 to 10 mg/ml and the effective amount of the MPL is from 0.1 to 10 mg/ml, and are combined in a ratio of from 1:1 to 1:20 for the aluminum hydroxide and the MPL to the WGP.

4. The composition of claim 2, wherein the effective amount of the aluminum hydroxide is from 0.1 to 10 mg/ml and the effective amount of the MPL is from 0.1 to 10 mg/ml of the MPL, and are combined in a ratio of from 1:1 to 1:20 for the aluminum hydroxide and the MPL to the WGP, and wherein the effective amount of the mannan is from 0.01 mg/ml to 1 mg/ml.

5. The composition of claim 2, wherein the effective amount of the mannan is from 0.01 mg/ml to 1 mg/ml.

6. A kit comprising the composition of claim 1 or claim 2 and instructions for use.

7. A method to augment innate immunity against a bacterium or a fungus in a mammalian subject comprising administering to the subject an effective amount of the composition of claim 1 or claim 2.

8. The method of claim 7, wherein the bacterium is selected from *S. aureus, A. baumannii, K. pneumoniae, P. aeruginosa, E. coli, Enterobacter* spp., *Serratia, Stenotrophomonas*, and the fungus is *Candida* spp.

9. The method of claim 7, wherein the subject is at risk of a bacterial infection or a fungal infection.

10. The method of claim 7, wherein the subject is infected with the bacterium or the fungus.

* * * * *